United States Patent [19]

Grayson

[11] Patent Number: 5,393,770
[45] Date of Patent: Feb. 28, 1995

[54] FUNGICIDAL COMPOSITIONS

[75] Inventor: Basil T. Grayson, Canterbury, England

[73] Assignee: Shell Research Limited, London, United Kingdom

[21] Appl. No.: 121,401

[22] Filed: Sep. 14, 1993

Related U.S. Application Data

[63] Continuation of Ser. No. 922,431, Jul. 30, 1992, abandoned.

[30] Foreign Application Priority Data

Jul. 31, 1991 [GB] United Kingdom ............... 9116557

[51] Int. Cl.$^6$ .................. A01N 43/50; A01N 43/64
[52] U.S. Cl. .................................. 514/383; 514/399
[58] Field of Search .............................. 514/383, 399

[56] References Cited

U.S. PATENT DOCUMENTS 3,930,010 12/1975 Klopping ............................ 514/388

FOREIGN PATENT DOCUMENTS 0267778 5/1988 European Pat. Off. .
2180236A 3/1987 United Kingdom .

OTHER PUBLICATIONS

Schaller et al., C.A.; vol. 69 (1968) 57623.

Primary Examiner—Allen J. Robinson
Attorney, Agent, or Firm—John W. Hogan, Jr.

[57] ABSTRACT

A fungicidal composition which comprises a compound of general formula:

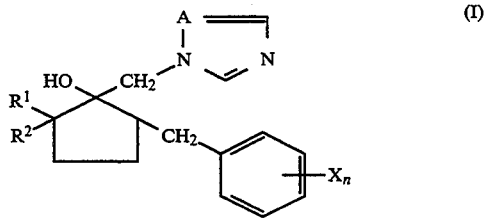

or acid addition salts or metal complexes thereof, wherein $R^1$ and $R^2$ each independently represents a $C_{1-5}$ alkyl group or a hydrogen atom; X represents a halogen atom, a $C_{1-5}$ alkyl group or a phenyl group; n is 0, 1 or 2 and A represents a nitrogen atom or CH; and an aliphatic alcohol alkoxylate, for example an ethoxylate, with an average of 5–9 ethylene oxide units per molecule, of a $C_{9-15}$ aliphatic alcohol, as adjuvant. It has been found that the presence of the alkoxylate substantially enhances the fungicidal efficacy of a compound of general formula I, in particular in foliar spray applications against fungi which are pathogenic to cereal crops.

7 Claims, No Drawings

FUNGICIDAL COMPOSITIONS

This is a continuation of application Ser. No. 922,431, filed Jul. 30, 1992, abandoned.

FIELD OF THE INVENTION

The present invention relates to fungicidal compositions, to their use in combating undesired fungal organisms, and to their preparation.

BACKGROUND OF THE INVENTION

The invention concerns, in particular, novel fungicidal compositions which incorporate benzyl triazolyl cyclopentane compounds which are disclosed in GB-A-2180236 and EP-A-267778.

SUMMARY OF THE INVENTION

It has now been discovered that the fungicidal activity of the aforementioned compounds is enhanced to a surprising and significant extent by the co-application to a plant to be treated, of an adjuvant selected from a particular class, namely aliphatic alcohol alkoxylates. Testing has revealed that although adjuvants of various classes cause some enhancement of activity the enhancement of activity caused by aliphatic alcohol alkoxylates is particularly interesting. The aliphatic alcohol alkoxylates as a class appear to stand apart from other adjuvants, consistently over a wide range of adjuvant and active ingredient application rates, while being substantially non-phytotoxic. Moreover, they are very suitable for the development of practical formulations.

DESCRIPTION OF THE INVENTION

In accordance with a first aspect of the present invention, there is provided a fungicidal composition which comprises a compound of general formula:

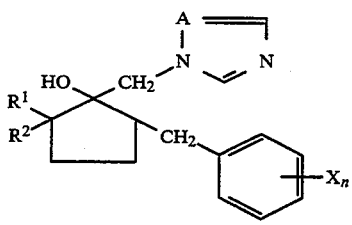

(I)

or acid addition salts or metal complexes thereof, wherein $R^1$ and $R^2$ each independently represents a $C_{1-5}$ alkyl group or a hydrogen atom; X represents a halogen atom, a $C_{1-5}$ alkyl group or a phenyl group; n is 0, 1 or 2 and A represents a nitrogen atom or CH; and an alkoxylate of an aliphatic alcohol.

In accordance with a second aspect of the present invention, there is provided a method of combating a fungus at a locus, comprising treating the locus with a composition of the invention.

In the method according to the invention, the locus may be an agricultural or horticultural locus, for example, plants subject to fungal attach, seeds of such plants or the medium in which plants are growing or are to be grown. The method may comprise combating a fungus already present at a locus and/or prophylactic fungicidal treatment at a locus. Preferably, the method according to the invention involves the foliar treatment of plants with the composition. The composition may be used to control a large number of fungal diseases of plants. Reference is made to the list on pages 36 to 37 of EP 267778, which list is incorporated herein by reference. In particular, the plants are suitably cereals, especially wheat or barley plants, because of the high level of control achieved by the method of the invention against infestations of the fungi *Erysiphe graminis* (powdery mildew) and *Leptosphaeria nodorum* (septoria).

Preferably, the method of the invention comprises treating the locus with an aqueous composition which comprises a compound of general formula I and an alkoxylate of an aliphatic alcohol.

A preferred alkoxylate of an aliphatic alcohol is based on alkoxy units having 2 carbon atoms, thus being a mixed ethoxylate, or 2 and 3 carbon atoms, thus being a mixed ethoxylate/propoxylate. An ethoxylate is preferred. Such alcohol alkoxylates are available from various sources or may be prepared by alkoxylating a suitable aliphatic alcohol under known conditions.

In preferred aliphatic alcohol alkoxylates for use in the present invention, the alkoxylate chain may have at least 5 alkoxy moieties, suitably from 5 to 25 alkoxy moieties, preferably from 5 to 15, and most preferably from 5 to 9.

In the alcohol alkoxylates of the present invention, the alcohol moiety is derived from a $C_{9-18}$ aliphatic alcohol, preferably a $C_{9-15}$ aliphatic alcohol. As is well known, such alcohols are normally available in the form of mixtures. However, in the context of the present invention, preferred alcohols are at least 50% by weight primary and at least 50% by weight straight chain alcohols and with at least 50% by weight having one hydroxy group. They may be saturated or unsaturated but the highest activity has been shown by alcoholates in which at least 50% by weight are saturated alcohol alkoxylates.

Good results have been obtained using alcohol alkoxylates in which the alcohol is of vegetable or animal oil origin. Good results have also been obtained using alcohol alkoxylates in which the alcohol is of mineral oil origin.

In the compositions of the invention the presence of an alkoxylate of an aliphatic alcohol substantially reduces the quantity of a compound of general formula I which needs to be applied to a locus to obtain a given level of activity. In practice, a compound of general formula I is suitably applied to a locus in an amount in the range of from 20 g/ha to 600 g/ha, preferably 50 g/ha to 300 g/has. The adjuvant is suitably applied to a locus in an amount in the range of from about 80 g/ha to about 2000 g/ha, preferably about 300 g/ha to about 1500 g/ha.

Although a composition comprising an aliphatic alcohol alkoxylate and a compound of general formula I may have other fungicidal indications, it is likely to be of primary benefit for therapeutic foliar applications. Activity can be enhanced or broadened by co-application of an additional fungicidal compound, suitable examples being dithianon, chlorothalonil and fenpropimorph. Preliminary tests have indicated that the enhancement effect which the alkoxylate adjuvant has on a compound of general formula I remains, when such an additional compound is also applied. Such an additional compound, when co-applied, may suitably be co-applied in an amount in the range of from 20 g/ha to 1200 g/ha, preferably 100 g/ha to 800 g/ha.

It may be desirable to co-apply further compound(s) to a said locus, for example an insecticide, acaricide, herbicide or nematocide, or a fertilizer.

In accordance with a further aspect of the present invention, there is provided an aqueous composition for use in the method of the invention to be applied to a said locus. Such a composition is prepared by mixing the aliphatic alcohol ethoxylate and a compound of general formula I, taken from separate sources, in water in a tank; or, preferably, by adding, to water in a tank, a premixed "one-pack" formulation containing both an aliphatic alcohol alkoxylate and a compound of general formula I. Such a premixed formulation is most conveniently in the form of a liquid or a wettable powder, the manufacture of each of which is entirely standard.

An antifoaming agent is employed, if desired, in accordance with standard practice. An antifoaming agent may be a constituent of a "one-pack" formulation. When the aqueous composition is to be prepared by mixing an aliphatic alcohol ethoxylate and a composition containing a compound of general formula I in a tank, and an antifoaming agent is desired, the antifoaming agent is conveniently formulated with the ethoxylate component.

Conventionally, antifoaming agents are selected on the basis of compatibility with the formulation to be prepared; thus, for example, solubility of the antifoamer in the formulation has to be determined. Selection on such a basis is entirely routine in formulation technology. It was expected that, if needed, for the compositions of the present invention, and especially for the "one-pack" formulations, compatible, conventional antifoaming agents, including silicone-based products, would be suitable. However, it has been found that conventional agents such as silicone-based products are in fact not suitable for use with the compositions of the present invention.

It has been found, however, that certain paraffinic oils, which are not conventional antifoaming agents, are not only compatible with compositions of the present invention but also provide useful antifoaming properties where needed. It is therefore preferred that the composition of the present invention is used in conjunction with a paraffinic oil as antifoaming agent, e.g., as an ingredient of the composition or by addition with the formulation ingredients when prepared in a tank mix with water.

Usually, paraffinic oils are derived from petroleum sources and are composed of paraffinic and aromatic, usually naphthenic, hydrocarbons. Suitable paraffinic oils for use as antifoaming agent with a composition of the present invention have a molecular weight in the range of from about 140 to about 180 and contain in the range of from 45% to 100% by weight, preferably 50% to 100% by weight, paraffinic hydrocarbons.

The concentration of the components in the aqueous composition are calculated from the amount of a compound of general formula I and of alkoxylate it is desired to supply, and the rate of application of the composition (that is, the volume applied per unit area). Typically, the rate of application of the composition may be in the range of from 100 l/ha to 1000 l/ha. Thus, when the rate of application of the composition is to be 1000 l/ha, and that of a compound of general formula I and of the alkoxylate, 100 g/ha and 400 g/ha, respectively, the aqueous composition will contain 0.1 g/l of a compound of general formula I and 0.4 g/l of alkoxylate. Generally, the aqueous composition may contain from 0.02 g/l to 6.0 g/l of a compound of general formula I and from 0.08 g/l to 20 g/l alkoxylate.

In accordance with a further aspect of the present invention, there is provided a concentrate formulation containing an alkoxylate of an aliphatic alcohol and of a compound of general formula I for dispersion or dissolution in water. Such a concentrate formulation may suitably contain from about 5 g/kg to about 200 g/kg, preferably from about 30 g/kg to 120 g/kg, of a compound of general formula I and from about 100 g/kg to about 1000 g/kg, preferably 400 g/kg to 700 g/kg, of adjuvant, the balance of the concentrate formulation being the usual types of additional materials. Useful formulations arise from a weight ratio of in the range of from about 5:1 to about 20:1, preferably from about 5:1 to about 10:1, of alkoxylate adjuvant to compound of general formula I.

With reference to compounds of general formula I, it will be appreciated that these will have optical isomers. Three optical centers can be present, or two are present when $R^1$ and $R^2$ are identical. The method of the invention may employ a compound of general formula I in the form of a single isomer, or in the form of a racemic mixture, or in the form of any other mixture of optical isomers.

For example, when $R^1$ and $R^2$ are identical, the following isomers may be present:

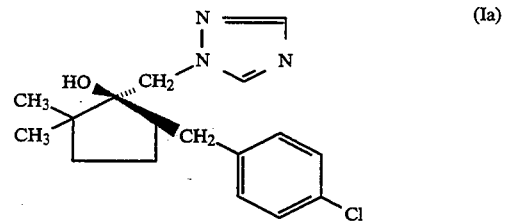

(Ia)

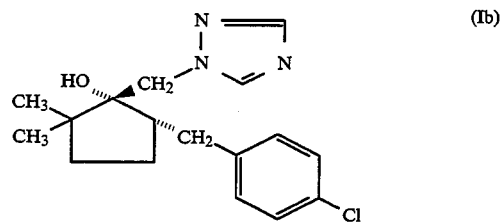

(Ib)

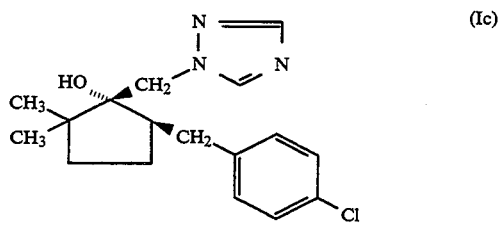

(Ic)

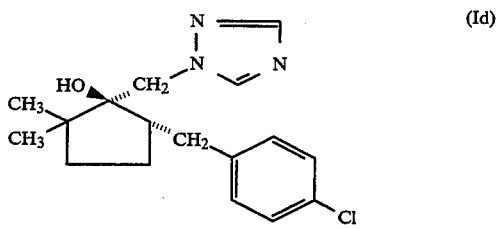

(Id)

Forms Ia and Ib are hereinafter referred to as the "cis" isomers. Forms Ic and Id are hereinafter referred to as the "trans" isomers. In using the terms "cis" and "trans", reference is thus being made to the relative positions of the hydroxy and halobenzyl groups.

Most preferably, a compound of general formula I is in the form of the "cis" isomers or a mixture of "cis" and "trans" isomers, in which "cis" isomers are at least 50% by weight. For the preparation thereof, reference is made to EP-A-357404 and EP-A267778, respectively.

Preferably, $R^1$ in a compound of general formula I represents a hydrogen atom or a $C_{1-4}$ alkyl group, and $R^2$ represents a hydrogen atom or a $C_{1-4}$ alkyl group. Most preferably, each of $R^1$ and $R^2$ represents a methyl group.

Preferably, A in a compound of general formula I represents a nitrogen atom.

Preferably, $X_n$ in a compound of general formula I represents a halogen atom, e.g., fluorine, chlorine or bromine, preferably chlorine, at the 4-position of the benzene ring. The term "n" is preferably 1.

The invention extends to a method for the preparation of a composition as described herein.

The invention will now be further described with reference to the accompanying Examples which should not be construed as limiting.

EXAMPLE 1 a) Materials

The following emulsifiable concentrate (EC) and suspension concentrate (SC) formulations of a compound of general formula I were prepared, the EC by blending the components and the SC by blending and milling the components in a bead mill.

The active ingredient (a.i.) used for Trials 1-5, described hereafter, of Example 1, was an 80/20 mixture of the "cis" isomers and the "trans" isomers (i.e., thought to be a 40/40/10/10 mixture of form Ia, Ib, Ic and Id) of the compound 1-(4-chlorobenzyl)-3,3-dimethyl-2-hydroxy-2-(1,2,4-triazol-1-yl)methylcyclopentane (i.e. compound of general formula I wherein $R^1=R^2=CH_3$, $X_n=4$-Cl, A=N).

The active ingredient used for Trials 6-7, described hereafter, of Example 1, was substantially the "cis" isomers, (thought to be a 50/50 mixture of forms Ia and Ib) of the same compound.

| Emulsifiable concentrate Composition: | | Suspension concentrate Composition: | |
|---|---|---|---|
| a.i. | 100 g | a.i. | 188 g |
| TENSIOFIX XN6 | 18 g | VANISPERSE | 25 g |
| TENSIOFIX XN10 | 42 g | KELZAN | 2.5 g |
| SURFADONE LP100 | 60 g | BEVALOID 642 | 1.0 g |
| N-butanol | 40 g | PROXEL GXL | 1.5 g |
| SHELLSOL A to | 1 l | Propylene glycol | 120 kg |
| | | Water (tap) to | 1 kg |

TENSIOFIX surfactants are emulsifiers, purchased from Omnichem Belgium.
SURFADONE LP100 is an n-octyl pyrrolidone solvent, from GAF Ltd.
SHELLSOL A is a solvent, trimethyl benzene, from Shell Chemical Co., Ltd.
VANISPERSE is a dispersant, a fractionated sodium salt of oxylignin, from Trafford Chemicals.
KELZAN is an industrial grade xanthan gum, from Merck & Co. or Kelco International.
BEVALOID 642 is an antifoaming agent, from Bevaloid Ltd.
PROXEL GXL is an aqueous dipropylene glycol solution of the preservative 1,2-benzisothiazolin-3-one, from ICI.

The following adjuvants were employed:
GENAPOL C-050, C-080, C-100 and C-200 which are alcohol ethoxylate adjuvants from Hoechst in which the alcohol moiety is derived from coconut oil, and the ethoxylate moiety has an average 5, 8, 10 or 20 ethylene oxide units per molecule, respectively.

Alcohols derived from coconut oil typically comprise the following components (ref. E. W. Eckey "Vegetable Fat & Oils", published by Reinhold Publishing Corp. 1954, New York)

| caprylic | ($C_8$) | 9.0% |
|---|---|---|
| capric | ($C_{10}$) | 6.8% |
| lauric | ($C_{12}$) | 46.4% |
| myristic | ($C_{14}$) | 18.0% |
| palmitic | ($C_{16}$) | 9.0% |

GENAPOL O series adjuvants, from Hoechst, correspond to GENAPOL C series but have oleyl/$C_{16-18}$ unsaturated alcohol moieties.
ATLAS G-1281—a polyoxyethylene fatty glyceride, from ICI.
ARKOPAL N-060, N-100 and N-230 which are $C_9$ alkyl phenol adjuvants from Hoechst, in which the ethoxylate moiety has an average 6, 10 and 23 ethylene oxide units per molecule, respectively.
HVI 60—a paraffinic oil adjuvant containing 100 g/l EMULSOGEN M, a castor oil ethoxylate from Hoechst.
DOBANOL alcohol ethoxylates, from Shell Chemical Co., Ltd. The nomenclature of the DOBANOL ethoxylates is such that DOBANOL 91, 23, 25 and 45 ethoxylates have $C_{9-11}$, $C_{12-13}$, $C_{12-15}$ and $C_{14-15}$ primary alcohol moieties, and the number after the hyphen denotes the average number of ethoxy units per molecule.

b) Plants

Wheat plants (*Triticum aestivum* cv Hornet and cv Norman) were grown to the 2-3 leaf stage under normal greenhouse propagation conditions (top watering; temperature, 20°-25° C.; lighting, 16 h photoperiod of daylight supplemented by mercury vapor/sodium lamps).

The variety (cv Hornet) was inoculated with dry *Erysiphe graminis fsp tritici* (powdery mildew) from diseased plants 1 day before spraying and held under greenhouse conditions until sprayed. The variety (cv Norman) was inoculated with *Leptosphaeria nodorum* (septora' glume blotch) using an aqueous suspension of spores washed from agar plates also 1 day before spraying. The inoculated plants were held at 21° C. under high humidity conditions for 18 h. They were then brought to greenhouse conditions and allowed to dry before being sprayed.

c) Preparation and application of spray solutions

Two series of adjuvants were tested in two trials, each conducted in the same manner. Aliquots (1.25, 0.63, 0.32, 0.16, 0.08, 0 ml) of the EC formulation and amounts (1.33, 0.66, 0.33, 0.16, 0.08, 0 g) of the SC formulation were each dispersed in tap water (250 ml). Amounts (2.5 g) of each adjuvant were also dispersed in tap water (250 ml). An aliquot (20 ml) of each formulation dispersion was mixed with an equal aliquot of adjuvant solution to give arrays of dispersions for each formulation type.

These dispersions were sprayed onto pairs of pots of each variety of wheat plants at a volume rate of 400 l/ha. At this rate and at the concentrations used, the applications were equivalent to 100, 50, 25, 12.5, 6.3 and 0 g/ha, respectively, of a.i. for the EC formulation and 200, 100, 50, 25, 12.5 and 0 g/ha, respectively, of a.i. for the SC formulation. The application rate of adjuvant was equivalent to 1 kg/ha.

d) Assessment

The sprayed plants were allowed to dry and returned to the greenhouse conditions given above, except that the watering was by automated sub-irrigation. Assessment of disease was by visual assay at 6–8 days (powdery mildew) or 8–10 days (septoria) after spraying. For septoria the extent of infection was assessed on a scale 0–9 (0=no infection, 9-sporulating lesions and necrotic tissue completely covering inoculated foliage). The assessment for powdery mildew was on a 0–9 scale, as for septoria, or was an estimate of the % area covered by sporulating lesions on the inoculated foliage.

The 0–9 scale is referred to in the Results as the "Infection Score".

e) Results

A series of seven trials were carried out as described above and Tables 1 to 17 contain the mean results of the two independent assessments of the leaves inoculated and sprayed for each treatment.

It will be observed that although all adjuvants tested gave some enhancement of activity of at least one combination of adjuvant application rate and active ingredient application rate, the only adjuvants which gave good enhancement at all combinations tested were the GENAPOL and DOBANOL alcohol ethoxylates.

Trial 1

Effect of adjuvants on the therapeutic control of 1-day old infections of powdery mildew on wheat

TABLE 1 a) EC formulation.

| ADJUVANT appln rate 1 Kg/ha | % LEAF AREA SPORULATING LESIONS a.i. application rate, g/ha | | | | | |
|---|---|---|---|---|---|---|
| | 0 | 6.3 | 12.5 | 25 | 50 | 100 |
| none | 73 | 58 | 40 | 28 | 13 | 7 |
| GENAPOL C-050 | 70 | 38 | 25 | 5 | 5 | 5 |
| GENAPOL C-080 | 65 | 40 | 10 | 9 | 6 | 10 |
| GENAPOL C-100 | 68 | 20 | 20 | 6 | 5 | 5 |
| GENAPOL C-200 | 55 | 30 | 23 | 9 | 6 | 5 |

TABLE 2 b) SC formulation.

| ADJUVANT appln rate 1 Kg/ha | % LEAF AREA SPORULATING LESIONS a.i. application rate, g/ha | | | | | |
|---|---|---|---|---|---|---|
| | 0 | 12.5 | 25 | 50 | 100 | 200 |
| none | 65 | 53 | 53 | 40 | 35 | 25 |
| GENAPOL C-050 | 75 | 20 | 13 | 10 | 7 | 10 |
| GENAPOL C-080 | 48 | 10 | 6 | 7 | 5 | 5 |
| GENAPOL C-100 | 68 | 20 | 15 | 9 | 9 | 6 |
| GENAPOL C-200 | 63 | 28 | 23 | 10 | 6 | 6 |

Trial 1

Effect of adjuvants on the therapeutic control of 1-day old infections of septoria on wheat

TABLE 3 a) EC formulation.

| ADJUVANT appln rate 1 Kg/ha | INFECTION SCORE a.i. application rate, g/ha | | | | | |
|---|---|---|---|---|---|---|
| | 0 | 6.3 | 12.5 | 25 | 50 | 100 |
| none | 7.5 | 5 | 3.5 | 1.5 | 1 | 0 |
| GENAPOL C-050 | 5.5 | 2 | 1 | 0 | 0 | 0 |
| GENAPOL C-080 | 6 | 1.5 | 0.5 | 1 | 0.5 | 1 |
| GENAPOL C-100 | 6 | 2 | 0.5 | 1 | 0.5 | 1.5 |
| GENAPOL C-200 | 6.5 | 3 | 2.5 | 1.5 | 1 | 1 |

TABLE 4 b) SC formulation.

| ADJUVANT appln rate 1 Kg/ha | INFECTION SCORE a.i. application rate, g/ha | | | | | |
|---|---|---|---|---|---|---|
| | 0 | 12.5 | 25 | 50 | 100 | 200 |
| none | 4.5 | 3 | 2.5 | 2 | 2.5 | 1 |
| GENAPOL C-050 | 4 | 1.5 | 0.5 | 0 | 0 | 0 |
| GENAPOL C-080 | 3.5 | 0.5 | 1 | 0 | 0 | 0.5 |
| GENAPOL C-100 | 5 | 1 | 1 | 0.5 | 0 | 1 |
| GENAPOL C-200 | 6 | 2 | 0.5 | 0 | 0.5 | 0.5 |

Trial 2

Effect of adjuvants on the therapeutic control of 1-day old infections of powdery mildew on wheat

TABLE 5 a) EC formulation.

| ADJUVANT appln rate 1 Kg/ha | % LEAF AREA SPORULATING LESIONS a.i. application rate, g/ha | | | | | |
|---|---|---|---|---|---|---|
| | 0 | 6.3 | 12.5 | 25 | 50 | 100 |
| none | 97.5 | 75 | 65 | 48 | 8 | 2 |
| ARKOPAL N-060 | 78 | 50 | 23 | 8 | 5 | 0 |
| ARKOPAL N-100 | 88 | 28 | 13 | 3 | 1 | 1 |
| ARKOPAL N-230 | 90 | 33 | 20 | 10 | 4 | 1 |
| Emulsified paraffin oil | 90 | 38 | 11 | 2 | 2 | 0 |

TABLE 6 b) SC formulation.

| ADJUVANT appln rate 1 Kg/ha | % LEAF AREA SPORULATING LESIONS a.i. application rate, g/ha | | | | | |
|---|---|---|---|---|---|---|
| | 0 | 12.5 | 25 | 50 | 100 | 200 |
| none | 90 | 80 | 68 | 65 | 45 | 55 |
| ARKOPAL N-060 | 75 | 28 | 5 | 0 | 1 | 0 |
| ARKOPAL N-100 | 83 | 20 | 4 | 2 | 1 | 1 |
| ARKOPAL N-230 | 93 | 9 | 3 | 1 | 0 | 0 |
| Emulsified paraffin oil | 93 | 9 | 3 | 1 | 0 | 0 |

Trial 2

Effect of adjuvants on the therapeutic control of 1-day old infections of septoria on wheat

TABLE 7 a) EC formulation.

| ADJUVANT appln RATE 1 Kg/ha | INFECTION SCORE a.i. application rate, g/ha | | | | | |
|---|---|---|---|---|---|---|
| | 0 | 6.3 | 12.5 | 25 | 50 | 100 |
| none | 8 | 7 | 6.5 | 5 | 1.5 | 0.5 |
| ARKOPAL N-060 | 8.3 | 6 | 4 | 4.5 | 1.3 | 3 |
| ARKOPAL N-100 | 8.5 | 5 | 2.8 | 3 | 2 | 3 |
| ARKOPAL N-230 | 8 | 4.3 | 3.5 | 2.8 | 2.5 | 3.3 |
| Emulsified paraffin oil | 8 | 3.3 | 1.5 | 1.3 | 1 | 1 |

TABLE 8 b) SC formulation.

| ADJUVANT appln rate 1 Kg/ha | INFECTION SCORE a.i. application rate, g/ha | | | | | |
|---|---|---|---|---|---|---|
| | 0 | 12.5 | 25 | 50 | 100 | 200 |
| none | 7.8 | 6.3 | 3.5 | 3.5 | 3.3 | 3.3 |
| ARKOPAL N-060 | 7.8 | 2.5 | 1.3 | 1 | 0.5 | 0.3 |
| ARKOPAL N-100 | 8.8 | 2.3 | 1.3 | 1 | 0.8 | 0.8 |
| ARKOPAL N-230 | 8.5 | 3.8 | 2.3 | 2 | 1 | 1.3 |
| Emulsified paraffin oil | 6.5 | 3 | 0.8 | 1.5 | 0.5 | 0.8 |

Trial 3

Effect of adjuvants on the therapeutic control of 1-day old infections of powdery mildew on wheat

TABLE 9 a) EC formulation.

| GENAPOL C-080 appln rate g/ha | % LEAF AREA SPORULATING LESIONS a.i. application rate, g/ha | | | | | |
|---|---|---|---|---|---|---|
| | 0 | 6.3 | 12.5 | 25 | 50 | 100 |
| 0 | 80 | 43 | 33 | 15 | 4 | 2 |
| 187 | 70 | 23 | 10 | 1 | 0 | 0 |
| 375 | 65 | 15 | 7 | 2 | 0 | 0 |
| 750 | 58 | 11 | 7 | 1 | 0 | 0 |
| 1500 | 55 | 11 | 6 | 0 | 0 | 0 |

TABLE 10 b) SC formulation.

| GENAPOL C-080 appln. rate g/ha | % LEAF AREA SPORULATING LESIONS a.i. application rate, g/ha | | | | | |
|---|---|---|---|---|---|---|
| | 0 | 6.3 | 12.5 | 25 | 50 | 100 |
| 0 | 83 | 68 | 40 | 35 | 25 | 38 |
| 187 | 73 | 15 | 5 | 3 | 1 | 0 |
| 375 | 55 | 12 | 5 | 2 | 0 | 0 |
| 750 | 55 | 14 | 2 | 1 | 0 | 0 |
| 1500 | 60 | 15 | 4 | 1 | 0 | 0 |

Trial 3

Effect of adjuvants on the therapeutic control of 1-day old infections of septoria on wheat

TABLE 11 a) EC formulation.

| GENAPOL C-080 appln rate g/ha | INFECTION SCORE a.i. application rate, g/ha | | | | | |
|---|---|---|---|---|---|---|
| | 0 | 6.3 | 12.5 | 25 | 50 | 100 |
| 0 | 7.5 | 8 | 5 | 3 | 2 | 2 |
| 187 | 7 | 3.3 | 3 | 2 | 0.8 | 1.3 |
| 375 | 7.5 | 3 | 2.5 | 1.3 | 1.5 | 0.8 |
| 750 | 6.3 | 3.3 | 2.5 | 1.8 | 0.8 | 1.0 |
| 1500 | 6.3 | 2.5 | 2.3 | 2 | 1 | 1.5 |

TABLE 12 b) SC formulation.

| GENAPOL C-080 appln rate g/ha | INFECTION SCORE a.i. application rate, g/ha | | | | | |
|---|---|---|---|---|---|---|
| | 0 | 6.3 | 12.5 | 25 | 50 | 100 |
| 0 | 7 | 6.5 | 6.3 | 6.3 | 6.5 | 5.8 |
| 187 | 7 | 3.3 | 3 | 1.5 | 1 | 1.8 |
| 375 | 6.8 | 3.8 | 3 | 2 | 1.8 | 1.3 |
| 750 | 7.5 | 4.5 | 1.8 | 1.5 | 0.5 | 1 |
| 1500 | 4.8 | 1.5 | 1.3 | 1 | 0.5 | 0.5 |

Trial 4

Effect of adjuvants on the therapeutic control of 1-day old infections of powdery mildew on wheat

TABLE 13

EC formulation.

| ADJUVANT | appln rate g/ha | % LEAF AREA SPORULATING LESIONS a.i. application rate, g/ha | | | | |
|---|---|---|---|---|---|---|
| | | 0 | 6.3 | 12.5 | 25 | 50 |
| none | — | 80 | 38 | 16 | 6 | 3 |
| GENAPOL C-080 | 250 | — | 13 | 6 | 2 | 0 |
| | 500 | — | 7 | 4 | 0 | 0 |
| | 1000 | — | 13 | 4 | 3 | 0 |
| | 1500 | 50 | 19 | 8 | 1 | 0 |
| ARKOPAL N-100 | 250 | — | 15 | 6 | 4 | 2 |
| | 500 | — | 15 | 5 | 4 | 1 |
| | 1000 | — | 15 | 5 | 3 | 2 |
| | 1500 | 50 | 13 | 8 | 3 | 0 |
| Emulsified paraffin oil | 250 | — | 38 | 5 | 1 | 0 |
| | 500 | — | 20 | 6 | 1 | 0 |
| | 1000 | — | 23 | 6 | 2 | 0 |
| | 1500 | 53 | 15 | 1 | 1 | 0 |

Trial 4

Effect of adjuvants on the therapeutic control of 1-day old infections of septoria on wheat

TABLE 14

EC formulation.

| ADJUVANT | appln rate g/ha | INFECTION SCORE a.i. application rate, g/ha | | | | |
|---|---|---|---|---|---|---|
| | | 0 | 6.3 | 12.5 | 25 | 50 |
| none | — | 7.3 | 6 | 3.3 | 1.5 | 0.5 |
| GENAPOL C-080 | 250 | — | 1.8 | 1 | 0.5 | 0 |
| | 500 | — | 1.3 | 0.8 | 0.3 | 0 |
| | 1000 | — | 1.3 | 1 | 0 | 0.3 |
| | 1500 | 7 | 1.3 | 0.5 | 0.8 | 0.5 |
| ARKOPAL N-100 | 250 | — | 5.3 | 2 | 1.3 | 0.8 |
| | 500 | — | 3.5 | 1.3 | 0.5 | 0.3 |
| | 1000 | — | 3 | 1.5 | 0.8 | 0.5 |
| | 1500 | 8 | 3.5 | 1.8 | 1 | 0.5 |
| Emulsified paraffin oil | 250 | — | 3.5 | 1 | 0.5 | 0.5 |
| | 500 | — | 5 | 1 | 0.8 | 0.5 |
| | 1000 | — | 3.5 | 1.3 | 0.5 | 0.8 |
| | 1500 | 8 | 4.5 | 0.8 | 0.8 | 0.5 |

Trial 5

Effect of adjuvants on the therapeutic control of 1-day old infections of powdery mildew on wheat

TABLE 15

EC formulation.

| ADJUVANT appln rate 500 g/ha | INFECTION SCORE a.i. application rate, g/ha | | | | | |
|---|---|---|---|---|---|---|
| | 0 | 6.3 | 12.5 | 25 | 50 | MEAN* |
| none | 8.2 | 7 | 5.5 | 3.5 | 2.5 | 4.6 |
| DOBANOL 91-5 | 7 | 2 | 2 | 1.7 | 0.7 | 1.6 |
| DOBANOL 91-8 | 7 | 4.2 | 1.7 | 0.6 | 0.1 | 1.7 |
| DOBANOL 23-6.3 | 6.5 | 2.2 | 2.2 | 1.7 | 0.2 | 1.6 |
| DOBANOL 25-7 | 7.5 | 3 | 1.7 | 0.5 | 0.5 | 1.4 |
| DOBANOL 25-9 | 7 | 5 | 1.7 | 0.2 | 0.1 | 1.8 |
| DOBANOL 45-7 | 6.5 | 1.7 | 2.2 | 1 | 0.4 | 1.3 |
| GENAPOL C-050 | 7 | 2.5 | 1.7 | 0.6 | 0.4 | 1.3 |
| GENAPOL C-080 | 7.5 | 3 | 2.5 | 0.6 | 0.5 | 1.7 |
| Emulsified paraffin oil | 8 | 4.2 | 2.5 | 1.4 | 0.5 | 2.2 |
| ATLAS G1281 | 7.5 | 4.2 | 3.5 | 3.7 | 1 | 3.1 |

*Mean value of all doses

Trial 6

Effect of different DOBANOL adjuvants on the therapeutic control of 1-day old infections of powdery mildew on wheat

TABLE 16

| ADJUVANT | | SC formulation. | | | | |
|---|---|---|---|---|---|---|
| | applicatn rate | INFECTION SCORE a.i. application rate, g/ha | | | | |
| NAME | g/ha | 0 | 6.3 | 12.5 | 25 | 50 | *MEAN |
| none | — | 8.8 | 8.5 | 8.5 | 9 | 9 | |
| DOBANOL 91-8 | 250 | — | 6.5 | 4.5 | 1.5 | 1 | 2.6 |
| | 500 | — | 5.5 | 2 | 1.3 | 0 | |
| | 1000 | — | 5 | 2 | 1.3 | 0 | |
| | 1500 | 8 | 5.5 | 2 | 2 | 0 | |
| DOBANOL 25-7 | 250 | — | 7 | 4.3 | 1.1 | 1.2 | 2.7 |
| | 500 | — | 7 | 4 | 0.1 | 0 | |
| | 1000 | — | 5.5 | 4.5 | 0.7 | 0 | |
| | 1500 | 8 | 3.5 | 2.5 | 0.1 | 0 | |
| DOBANOL 45-7 | 250 | — | 6 | 4 | 0.8 | 0.3 | 1.9 |
| | 500 | — | 6 | 1.5 | 0.1 | 0 | |
| | 1000 | — | 4 | 0.8 | 0.1 | 0 | |
| | 1500 | 7.5 | 5.5 | 1.5 | 0.3 | 0.1 | |

*Over all a.i. concentrations and adjuvant application rates

Trial 7

Effect of different adjuvants on the therapeutic control of 1-day old infections of powdery mildew on wheat

TABLE 17

| ADJUVANT | | SC formulation. | | | | |
|---|---|---|---|---|---|---|
| | appln. rate | INFECTION SCORE a.i. application rate, g/ha | | | | |
| NAME | g/ha | 0 | 6.3 | 12.5 | 25 | 50 |
| None | — | 9 (0) | 9 (0) | 8.6 (0.5) | 8.6 (0.5) | 8.8 (0.3) |
| DOBANOL 91-6 | 250 | — | 7.8 (0.5) | 7.3 (0.9) | 5.9 (0.9) | 3 (0) |
| DOBANOL 91-6 | 500 | — | 5.9 (0.6) | 4 (2.4) | 1 (0.3) | 0.3 (0.2) |
| DOBANOL 91-6 | 750 | 8.8 (0.3) | 6 (1.2) | 2.9 (2) | 0.4 (0.2) | 0.1 (0.1) |
| DOBANOL 91-8 | 250 | — | 7.4 (0.5) | 5.5 (1) | 2.6 (1.1) | 1.1 (1.8) |
| DOBANOL 91-8 | 500 | — | 7.4 (0.9) | 3.8 (1.5) | 1.8 (1) | 0 (0) |
| DOBANOL 91-8 | 750 | 9 (0) | 7.5 (0.6) | 3.5 (0.6) | 1.1 (0.7) | 0.1 (0) |
| DOBANOL 23-63 | 250 | — | 6.5 (0.6) | 4.5 (0.6) | 5.3 (1) | 2.6 (0.9) |
| DOBANOL 23-63 | 500 | — | 6.8 (0.5) | 3.6 (1.5) | 0.6 (0.3) | 0.5 (0.4) |
| DOBANOL 23-63 | 750 | 8.9 (0.3) | 6.9 (1.0) | 3.8 (1.5) | 0.9 (0.2) | 0.1 (0.1) |
| DOBANOL 45-7 | 250 | — | 7.5 (0.4) | 4.8 (0.5) | 1.8 (1) | 0.3 (0.2) |
| DOBANOL 45-7 | 500 | — | 5.9 (1.3) | 3.8 (1.3) | 0.6 (0.3) | 0.1 (0.1) |
| DOBANOL 45-7 | 750 | 8.9 (0.3) | 7.3 (0.3) | 5.5 (1.7) | 1.1 (0.6) | 0.1 (0.1) |
| GENAPOL O-050 | 250 | — | 8.6 (0.5) | 8.4 (0.6) | 7.5 (0.6) | 7 (0) |
| GENAPOL O-050 | 500 | — | 8.8 (0.3) | 8 (0) | 7 (0.8) | 5 (0.2) |
| GENAPOL O-050 | 750 | 9 (0) | 8.8 (0.3) | 7.8 (0.3) | 6.8 (1.3) | 3 (0.8) |

( ) - Standard deviations
In this trial, results are the means of four replicate pots of plants.

EXAMPLE 2 a) Materials

The suspension concentrate (SC) used corresponded to that described above in Example 1. An emulsifiable concentrate (EC) similar to that described above in Example 1, was prepared, having the following composition.

| Emulsifiable Concentrate Composition: | |
|---|---|
| a.i. | 100 g |
| TENSIOFIX NS | 64 G |
| TENSIOFIX GS | 16 G |
| SURFADONE LP100 | 70 G |
| N-butanol | 40 g |
| SHELLSOL A to | 1 l. |

In each case the active ingredient consisted essentially of the "cis" isomers, as used for Trials 6 to 7 of Example 1.

The SC and EC formulations used in Example 2 were used as such, for comparison purposes, and were mixed with adjuvants including alcohol ethoxylates. In some cases, the SC or EC formulation, and the adjuvant(s), were separately added to water in a spray tank to form "tank-mix" formulations. In other cases the SC or EC formulation and the adjuvant(s) were mixed together to form pre-mixed "one-pack" formulations, to be added to water in a spray tank.

"One pack" soluble liquid (SL) compositions were prepared, having the following compositions:

| Ingredient | SL (1) | SL (2) | SL (3) | SL (4) |
|---|---|---|---|---|
| a.i | 100 | 80 | 60 | 40 |
| DOBANOL 91-6 | — | 600 | 600 | 600 |
| DOBANOL 23-6.5 | 500 | — | — | — |
| NMP* | 300 | — | — | — |
| Amyl alcohol | to 1 l. | to 1 l. | to 1 l. | to 1 l. |

*NMP: N-methyl pyrrolidone

In other, comparative SL compositions, the DOBANOL adjuvants were replaced with other adjuvants.

Most of the adjuvants used are described in Example 1. Other adjuvants described in this Example 2 are:
corn oil emulsifiable concentrate
ARMOBLEN 557, an alkylamine ethoxylate/-propoxylate, from Akzo.

Further "tank-mix" formulations were prepared by adding a second active ingredient to "tank-mix" formulations containing the SC composition described above and an alcohol ethoxylate adjuvant. The second active ingredients were dithianon (available from Shell Chemical Co., Ltd. under the Trademark DELAN), fenpropimorph (available from B.A.S.F. under the Trademark CORBEL) and chlorothalonil (available from B.A.S.F. under the Trademark BRAVO).

b) Plants

Winter wheat seeds, cv Hornet, were sown in 7 cm square pots. This resulted in establishment of 20 to 25 plants per pot. After 12 days under normal greenhouse conditions as described above, when the seedlings were at the 1-2 leaf stage, the plants were inoculated with *Erysiphe graminis fsp tritici* from a stock infection. Treatments were applied on day 13, usually about 28 hours after inoculation. Plants were then laid out in a controlled environment compartment of a greenhouse using a randomized double-block design to reduce variation due to placement. Watering was carried out by means of an automated sub-irrigation matting system.

c) Preparation and application of Spray solutions

All test solutions were sprayed at four doses, the difference between doses being a factor of 2, usually 12.5, 25, 50 and 100 g/ha, respectively, of a.i.. A single quantity of each product was weighed out for all of the doses of that product. When adjuvant was added as a single a.i.: adjuvant ratio, the whole batch was prepared for the highest dose, and then appropriate aliquots were diluted with tap water to the correct concentrations for the lower doses. When adjuvant was added at a single dose per hectare for all treatments, the base formulation was made up at double the required concentration and then each was dose diluted to the correct concentration using a stock solution of the adjuvant. All applications were made using a moving track sprayer fitted with a single flat-fan nozzle calibrated to give 400 l/ha of spray. Four pots (replicates) were sprayed with each treatment.

d) Assessment

Estimates of infection were made, in some cases after about one week, then after about two weeks if the results were of further interest. Usually the initial assessment was a score on a 0 to 9 scale, where 0=no infection and 9=very high infection of inoculated leaves. Later assessments were usually of percentage of leaf area infected by the mildew.

e) Results

The results are presented in tabular form in the following pages and information particular to the particular test is presented above the appropriate Table.

(i) Example 2, Results 1

Table 18 below presents the mean results of three series of tests intended to test the comparative efficacies of the adjuvants GENAPOL O-050, GENAPOL C-080, ATLAS G1281, and HVI 60 paraffinic oil containing 100 g/l EMULSOGEN M. The SC and EC lines relate to the efficacy of spray compositions derived from the SC and. EC formulations described above, without adjuvants.

The first series of tests employed a "tank-mix" with the SC. The second series of tests employed a "tank-mix" with the EC. The third series of tests employed "one-pack" formulations. In each case the adjuvant: active ingredient ratio was 10:1 (w:w).

Assessment was made 7 days after treatment.

TABLE 18

| ADJUVANT TESTED SCORES OF INFECTION | G/ha a.i. | | | |
|---|---|---|---|---|
| | 12.5 | 25 | 50 | 100 |
| SC (none) | 8 | 8 | 8.1 | 8 |
| EC (none) | 8 | 7 | 5.8 | 2.9 |
| HVI 60 Paraffinic Oil | 7.6 | 4.5 | 2.6 | 1.2 |
| ATLAS G1281 | 6.1 | 4.5 | 3.0 | 1.1 |
| GENAPOL O-050 | 5.8 | 4 | 2.9 | 0.2 |
| GENAPOL O-080 | 3.9 | 1.6 | 0.8 | 0.2 |

(ii) Example 2, Results 2

Table 19 presents the mean results of a series of tests showing the comparative efficacies of various adjuvants. The spray compositions were derived from "one-pack" formulations, coded as follows:

a—EC described above
b—EC containing corn oil adjuvant
c—EC containing HVI 60
d—EC containing ARMOBLEN 557
e—SL containing DOBANOL 91-6
f—SL containing GENAPOL C-080.

In each case the adjuvant:active ingredient ratio was 10:1 (W:W).

Assessment was made 7 days after treatment.

TABLE 19

| ADJUVANT TESTED SCORES OF INFECTION | G/ha a.i. | | | |
|---|---|---|---|---|
| | 12.5 | 25 | 50 | 100 |
| a | 6.5 | 6.2 | 4.6 | 2.5 |
| b | 6 | 3 | 1.3 | 0.7 |
| c | 4.1 | 1.4 | 1.1 | 0.7 |
| d | 3.8 | 2.9 | 1.3 | 0.7 |
| e | 3.5 | 0.8 | 0.8 | 0.8 |
| f | 2.8 | 1.6 | 1.1 | 1.0 |

(iii) Example 2, Results 3

Tables 20(a) and 20(b) below present the mean results of a series of tests intended to test the efficacy of HVI-60 paraffinic oil adjuvant and DOBANOL 91-6 alcohol ethoxylate adjuvant over a range of active ingredient and adjuvant application rates. The formulations to be diluted for spraying were prepared as "one-pack" formulations, the HVI-60 with the EC formulation Table 20a and the DOBANOL 91-6 with the SL formulation (Table 20b). Assessment was made 7 days after treatment.

The abbreviations used in Tables 20(a) and 20(b) are the following:

a—EC
b—a.i.: HVI in 1:5 by weight ratio
c—a.i.: HVI in 1:10 by weight ratio
d—a.i.: HVI in 1:20 by weight ratio TABLE 20(a)

| ADJUVANT TESTED SCORES OF INFECTION | G/ha a.i. | | | |
|---|---|---|---|---|
| | 12.5 | 25 | 50 | 100 |
| a | 7.2 | 6.3 | 3.9 | 1.9 |
| b | 6.2 | 2.2 | 0.5 | 0.5 |
| c | 5.3 | 2 | 1.7 | 0.3 |
| d | 5.2 | 1.6 | 0.5 | 0.3 |

TABLE 20(b)

| ADJUVANT TESTED SCORES OF INFECTION | G/ha a.i. | | | |
|---|---|---|---|---|
| | 12.5 | 25 | 50 | 100 |
| a | 7.2 | 6.3 | 3.9 | 1.9 |
| e | 4 | 2.2 | 1 | 0.2 |
| f | 3.7 | 1.2 | 0.3 | 0.2 |
| g | 2.1 | 0.4 | 0.3 | 0.2 |

(iv) Examples 2, Results 4

Tables 21(a) and 21(b) below present the mean results, 7 days after treatment and 14 days, respectively, after treatment, following testing of various "tank-mix" compositions, employing the SL formulations with an adjuvant: a.i ratio of 10:1 by weight.

The abbreviations used in the Tables 21(a) and 21(b) are the following:

S=SL
d=DELAN
b=BRAVO
c=CORBEL

TABLE 21(a)

| ADJUVANT TESTED SCORES OF INFECTION | G/ha a.i. | | | |
|---|---|---|---|---|
| | 13 | 26 | 52.5 | 105 |
| S | 2.5 | 1.1 | 0.2 | 0.2 |
| S + b | 1.3 | 0.8 | 0.2 | 0.1 |
| S + d | 0.8 | 0.2 | 0.2 | 0.2 |
| S + c | ~0 | ~0 | ~0 | ~0 |

TABLE 21(b)

| ADJUVANT TESTED ESTIMATED MILDEW INFECTION, % | G/ha a.i. | | | |
| --- | --- | --- | --- | --- |
| | 13 | 26 | 52.5 | 105 |
| S | 28 | 18 | 13 | 12 |
| S + b | 18 | 14 | 16 | 13 |
| S + d | 15 | 12 | 9 | 10 |
| S + c | 10 | 9 | 11 | 9 |

(v) Example 2, Results 5

Table 22 below presents the mean results, 7 days after treatment, of testing various spray compositions, with different a.i. and adjuvant application rates, derived from "one-pack" SL formulations of DOBANOL 91-6. Assessment was made 7 days after treatment.

The abbreviations used in Table 22 are the following:
a=EC
b=a.i.: DOBANOL in 1:5 by weight ratio
c=a.i.: DOBANOL in 1:10 by weight ratio
d=a.i.: DOBANOL in 1:7.5 by weight ratio
e=a.i.: DOBANOL in 1:20 by weight ratio
f=a.i.: DOBANOL in 1:15 by weight ratio

TABLE 22

| ADJUVANT TESTED SCORES OF INFECTION | G/ha a.i. | | | |
| --- | --- | --- | --- | --- |
| | 12.5 | 25 | 50 | 100 |
| a | 6.2 | 5 | 4.6 | 2 |
| b | 6.1 | 3.3 | 0.5 | 0.2 |
| c | 4.3 | 2.7 | 0.3 | 0.3 |
| d | 3.6 | 2.6 | 0.5 | 0.2 |
| e | 2.9 | 1 | 0.3 | 0.2 |
| f | 2.8 | 0.4 | 0.3 | 0.2 |

It should be noted that the use of capital letters in this specification to denote terms for materials indicates that those terms are, or are thought to be, trademarks in the country of their origin.

What is claimed is:

1. A fungicidal composition which comprises a compound of formula (I)

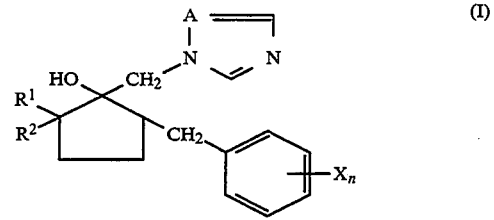

or the acid addition salts thereof, wherein $R^1$ and $R^2$ each independently represents a $C_{1-5}$ alkyl group or a hydrogen atom; X represents a halogen atom, a $C_{1-5}$ alkyl group or a phenyl group; n is an integer of 0, 1 or 2; and A represents a nitrogen, atom or CH; and an alkoxylate of an aliphatic alcohol said alkoxylate being an ethoxylate or a mixed ethoxylate/propoxylate comprised of 5 to 25 alkoxy moieties wherein the enhanced weight ratio of the alkoxylate to the compound of Formula I is from about 5:1 to about 20:1.

2. A composition as claimed in claim 1, wherein the alkoxylate comprises 5 to 9 alkoxy moieties.

3. A composition of claim 1 wherein the aliphatic alcohol is a $C_{9-18}$ aliphatic alcohol.

4. A composition of claim 1 wherein $R^1$ and $R^2$ both represent a methyl group, A represents a nitrogen atom and $X_n$ represents a 4-chloro atom.

5. A composition as claimed in claim 4 wherein the active ingredient consists of or predominantly comprises isomers in which the hydroxy and the halobenzyl moieties are arranged "cis" to each other.

6. A fungicidal composition of claim 1, being a concentrate formulation for addition to water, and containing from about 5 g/kg to about 200 g/kg of a compound of formula I, and in the range of from 100 g/kg to 500 g/kg of an alkoxylate of an aliphatic alcohol.

7. A method of combatting a fungus at a locus, which method comprises treating the locus with the formulation of claim 1 wherein the compound of Formula I is applied to the locus in an amount from about 50 g/ha to about 300 g/ha, and the alkoxylate, in an amount in the range of from about 300 g/ha to about 1500 g/ha.

* * * * *